(12) United States Patent
Chaudhari et al.

(10) Patent No.: US 10,251,850 B2
(45) Date of Patent: Apr. 9, 2019

(54) PROCESS FOR PREPARATION OF CYSTEAMINE BITARTRATE

(71) Applicant: LUPIN LIMITED, Mumbai, Maharashtra (IN)

(72) Inventors: Pankaj Ramchandra Chaudhari, Maharashtra (IN); Sukhdeo Sampat Gunjal, Maharashtra (IN); Raju Muktaji Walunj, Maharashtra (IN); Anurag Trivedi, Maharashtra (IN); Rajinder Singh Siyan, Maharashtra (IN); Nandu Baban Bhise, Maharashtra (IN); Girij Pal Singh, Maharashtra (IN)

(73) Assignee: LUPIN LIMITED, Mumbai, Maharashtra (IN)

( * ) Notice: Subject to any disclaimer, the term of this patent is extended or adjusted under 35 U.S.C. 154(b) by 0 days.

(21) Appl. No.: 15/868,284

(22) Filed: Jan. 11, 2018

(65) Prior Publication Data

US 2018/0193292 A1 Jul. 12, 2018

(30) Foreign Application Priority Data

Jan. 11, 2017 (IN) .............................. 201721001215
Oct. 17, 2017 (IN) .............................. 201721036899

(51) Int. Cl.
*C07C 59/245* (2006.01)
*A61K 31/145* (2006.01)
*A61K 31/095* (2006.01)
*C07C 323/25* (2006.01)
*C07C 319/12* (2006.01)
(Continued)

(52) U.S. Cl.
CPC .......... *A61K 31/145* (2013.01); *A61K 31/095* (2013.01); *C07C 59/245* (2013.01); *C07C 319/12* (2013.01); *C07C 323/25* (2013.01); *G01N 30/88* (2013.01); *C07B 2200/13* (2013.01); *G01N 23/20075* (2013.01); *G01N 30/02* (2013.01); *G01N 2030/027* (2013.01); *G01N 2223/056* (2013.01)

(58) Field of Classification Search
None
See application file for complete search history.

(56) References Cited

FOREIGN PATENT DOCUMENTS

WO  2007/089670 A2  8/2007
WO  2014/204881 A1  12/2014

OTHER PUBLICATIONS

Cysteamine Bitartrate MSDS (Capot Chemicals, 2016, Material Safety Data Sheet).*

* cited by examiner

*Primary Examiner* — Sudhakar Katakam
*Assistant Examiner* — Jennifer C Sawyer
(74) *Attorney, Agent, or Firm* — Merchant & Gould P.C.

(57) ABSTRACT

The present invention provides process for preparation of cysteamine bitartrate comprising reacting cysteamine or its salt with tartaric acid. The present invention further provides crystalline form L1 of cysteamine bitartrate having characteristic diffraction peaks at 10.36, 14.54, 17.23, 18.03, 19.24, 20.76, 21.20, 22.02, 23.37, 23.64, 27.71, 28.28, 29.26, 31.33, 32.84, 33.83, 35.51, 36.74±0.2 degree two theta in an X-ray diffraction pattern and process for preparation thereof. The present invention provides crystalline form L2 of cysteamine bitartrate having characteristic diffraction peaks at 7.4, 10.3, 11.0, 11.4, 14.4, 14.9, 18.6, 19.4, 20.1, 20.8, 21.9, 22.3, 22.5, 23.5±0.2 degree two theta in an X-ray diffraction pattern and process for preparation thereof.

4 Claims, 2 Drawing Sheets

(51) Int. Cl.
*G01N 30/88* (2006.01)
*G01N 30/02* (2006.01)
*G01N 23/20* (2018.01)

PROCESS FOR PREPARATION OF CYSTEAMINE BITARTRATE

FIELD OF THE INVENTION

The present invention relates to process for preparation of cysteamine bitartrate and novel crystalline forms L1 and L2 of cysteamine bitartrate.

BACKGROUND OF THE INVENTION

Cysteamine bitartrate (I) is a cystine depleting agent which lower the cystine content of cells in patients with cystinosis, an inherited defect of lysosomal transport, it is indicated for the management of nephropathic cystinosis in children and adults. Cysteamine bitartrate (I) is simplest stable aminothiol salt and has the following structural formula:

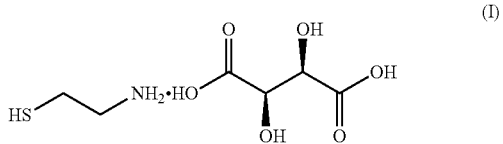

(I)

The application WO 2014204881 provides pharmaceutical composition of cysteamine bitrate and another application WO 2007089670 provides method of administrating cysteamine and pharmaceutically salts and method of treatment thereof.

The present invention provides process for preparation of cysteamine bitartrate and crystalline forms of cysteamine bitartrate and process for preparation thereof.

SUMMARY OF THE INVENTION

The present invention provides process for preparation of cysteamine bitartrate comprising reacting cysteamine or its salt with tartaric acid. The present invention further provides crystalline form L1 of cysteamine bitartrate having characteristic diffraction peaks at 10.36, 14.54, 17.23, 18.03, 19.24, 20.76, 21.20, 22.02, 23.37, 23.64, 27.71, 28.28, 29.26, 31.33, 32.84, 33.83, 35.51, 36.74±0.2 degree two theta in an X-ray diffraction pattern and process for preparation thereof. The present invention provides crystalline form L2 of cysteamine bitartrate having characteristic diffraction peaks at 7.4, 10.3, 11.0, 11.4, 14.4, 14.9, 18.6, 19.4, 20.1, 20.8, 21.9, 22.3, 22.5, 23.5±0.2 degree two theta in an X-ray diffraction pattern and process for preparation thereof.

DETAILED DESCRIPTION OF THE INVENTION

Figure 1:
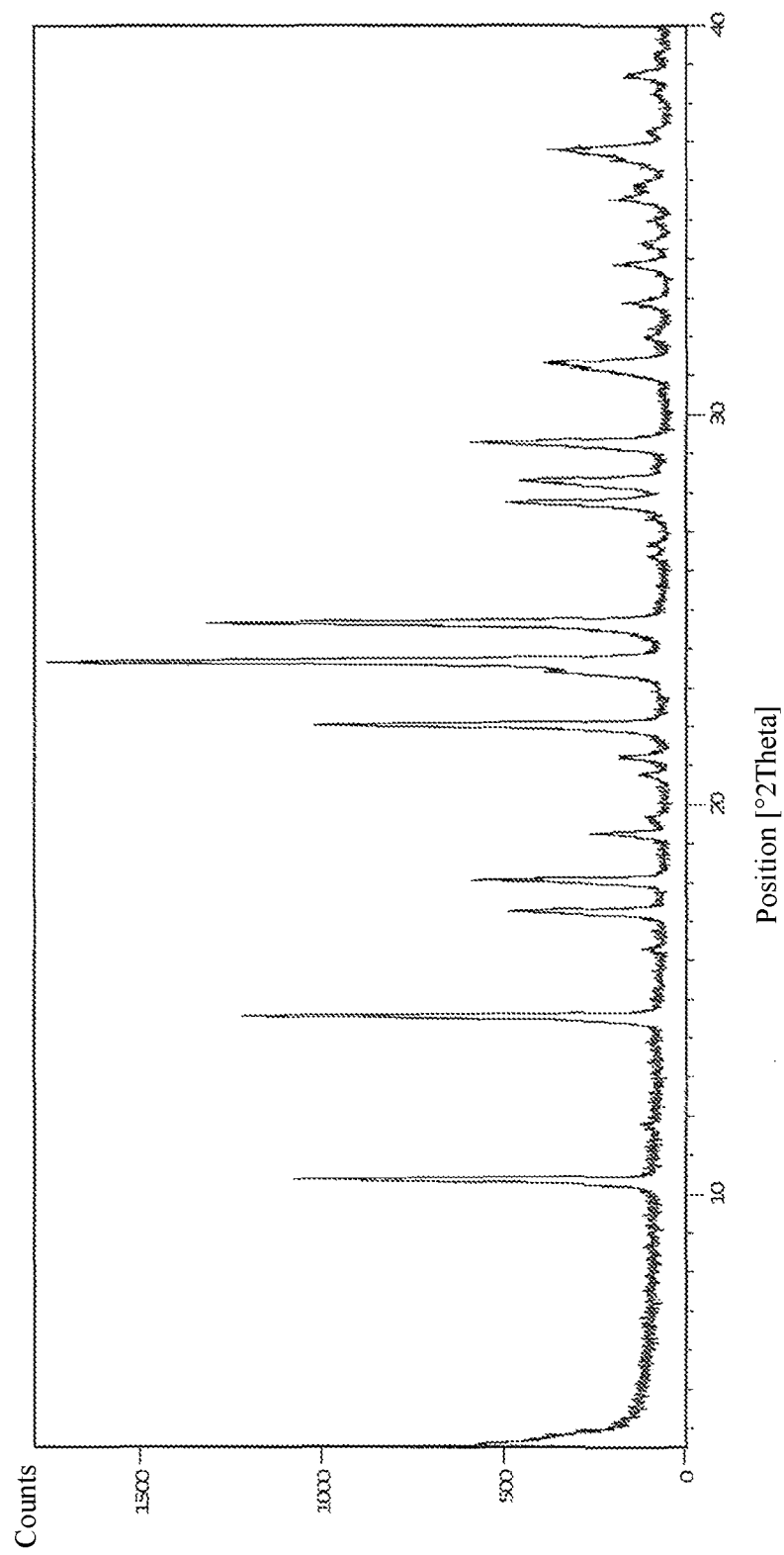
FIG. 1—X-ray powder diffraction pattern of crystalline form L1 of cysteamine bitartrate.

In one embodiment the present invention provides process for preparation of cysteamine bitartrate comprising reacting cysteamine or its salt with tartaric acid.

The cysteamine salt can be selected from inorganic or organic salt except tartaric acid. Inorganic salt can be selected from hydrochloride, hydrobromide, hydroiodide and the like. Organic salt can be selected from fumarate, propionate, butyrate, valerate, oxalate, maleate, citrate, glutarate, succinate, salicylate and the like.

The process for preparation of cysteamine bitartrate can be carried out in presence of solvent. The solvent can be selected from organic polar solvent, water or mixtures thereof. Polar solvent can be selected from alcohols like methanol, ethanol, butanol, propanol; nitriles like acetonitrile, propionitrile, butyronitrile; ethers like tetrahydrofuran, dioxane, dimethoxyethane; esters like ethyl acetate, ethyl acetoacetate, butyl acetate, propyl acetate; ketones like acetone, methyl ethyl ketone, methyl isobutyl ketone; other polar solvents like dimethylformamide, dimethyl sulfoxide, water and mixtures thereof.

The process for preparation of cysteamine bitartrate can be carried out optionally in presence of an antioxidant selected from butylated hydroxy anisole, butylated hydroxy toluene, and the like. The process for preparation of cysteamine bitartrate can be carried out at a temperature of 20° to 100° C.

Cysteamine bitartrate can be isolated from the reaction mixture by techniques known in art like filtration, concentration, removal of solvent by evaporation, distillation, centrifugation, cooling, flash evaporation, drying on rotavapor.

The isolated cysteamine bitartrate has a HPLC purity of greater than 90%, preferably greater than 95%, more preferably greater than 98%.

In another embodiment the present invention provides process for purification of cysteamine bitartrate with HPLC purity greater than 98%, comprising:
a) dissolving cysteamine bitartrate in a solvent,
b) cooling the mixture, and
c) isolating pure cysteamine bitartrate from the mixture.

Cysteamine bitartrate can be dissolved in a solvent selected from organic polar solvent, water or mixtures thereof. Polar solvent can be selected from alcohols like methanol, ethanol, butanol, propanol; nitriles like acetonitrile, propionitrile, butyronitrile; ethers like tetrahydrofuran, dioxane, dimethoxyethane; esters like ethyl acetate, ethyl acetoacetate, butyl acetate, propyl acetate; ketones like acetone, methyl ethyl ketone, methyl isobutyl ketone; other polar solvents like dimethylformamide, dimethyl sulfoxide, water and mixtures thereof.

Cysteamine bitartrate can be dissolved in the solvent by stirring the mixture at room temperature or upto the reflux temperature of the solvent. The pure cysteamine bitartrate can be isolated from the mixture by cooling the mixture to a temperature of below 30° C., preferably below 0° C., more preferably below −20° C.

Pure cysteamine bitartrate can be isolated from the reaction mixture by techniques known in art like filtration, concentration, removal of solvent by evaporation, distillation, centrifugation, cooling, flash evaporation, drying on rotavapor.

Pure cysteamine bitrate refers to cysteamine bitrate with a HPLC purity of greater than 98%, preferably greater than 99%, more preferably greater than 99.9%.

The process for preparation of cysteamine bitrate and process for its purification can be carried out under nitrogen atmosphere.

In yet another embodiment the present invention provides novel crystalline form L1 of cysteamine bitartrate. The crystalline form L1 of cysteamine bitartrate of the present invention is characterized by X-ray powder diffraction pattern as depicted in FIG. 1.

The crystalline form L1 of cysteamine bitartrate having characteristic diffraction peaks at 10.36, 14.54, 17.23, 18.03, 19.24, 20.76, 21.20, 22.02, 23.37, 23.64, 27.71, 28.28, 29.26, 31.33, 32.84, 33.83, 35.51, 36.74±0.2 degree two theta in an X-ray diffraction pattern. The X-ray powder diffraction pattern was recorded at room temperature using PANalytical X'Pert PRO diffractogram with Cu Kα radiation ($\lambda$=1.54060 Å), running at 45 kV and 40 mA.

The crystalline form L1 of cysteamine bitartrate having characteristic infrared absorption at 3321, 2975, 2495, 1872, 1730, 1586, 1411, 1336, 1304, 1263, 1213, 1134±2 cm-1. The infrared absorption spectrum was obtained using a Perkin Elmer Precisely Spectrum 400 instrument using KBr pellet method.

The crystalline form L1 of cysteamine bitartrate having characteristic differential scanning calorimetry peak at about 75.5° C. The Differential Scanning Calorimetry thermogram was obtained using Perkin Elmer Diamond DSC instrument with open pan. The sample was heated from 30° C. to 250° C. at a 10° C./min.

In a further embodiment, the present invention provides a process for the preparation of crystalline form L1 of cysteamine bitartrate comprising the steps of:
a) dissolving cysteamine bitartrate in a solvent,
b) optionally adding seed material,
c) cooling the mixture, and
d) isolating form L1 of cysteamine bitartrate from the mixture.

Solvents can be selected from organic polar solvent, water or mixtures thereof. Polar solvent can be selected from alcohols like methanol, ethanol, butanol, propanol; nitriles like acetonitrile, propionitrile, butyronitrile; ethers like tetrahydrofuran, dioxane, dimethoxyethane; esters like ethyl acetate, ethyl acetoacetate, butyl acetate, propyl acetate; ketones like acetone, methyl ethyl ketone, methyl isobutyl ketone; other polar solvents like dimethylformamide, dimethyl sulfoxide, water and mixtures thereof.

Cysteamine bitartrate can be dissolved in solvent by heating the mixture of Cysteamine bitartrate and the solvent to a temperature of 25° C. to reflux temperature. The seed material can be added at a temperature of 0 to 15° C. The mixture is cooled to a temperature of below 0° C., preferably below −10° C., more preferably below −20° C.; for a period ranging from 30 to 180 minutes and crystalline form L1 of cysteamine bitartrate can be isolated by techniques known in art like filtration, concentration, removal of solvent by evaporation, distillation, cooling, flash evaporation, drying on rotavapor. The solid is dried under 800-900 mm/Hg of vacuum at a temperature of less than 35° C. for a period of 2-24 hours.

It has been observed that crystalline form L1 of cysteamine bitartrate is stable and do not get converted to any other polymorphic form over a period of time and the impurity profile also remains consistent in the hold time study. The crystalline form L1 of cysteamine bitartrate was found to be stable at −20±5° C.; 5±3° C.; 25±2° C./60±5% RH; 30±2° C./65±5% RH and 40±2° C./75±5% RH. The HPLC purity of crystalline form L1 of cysteamine bitartrate was found to be in the range of 99.2% to 99.7% after one months of stability in the above mentioned stability parameters.

Figure 2:
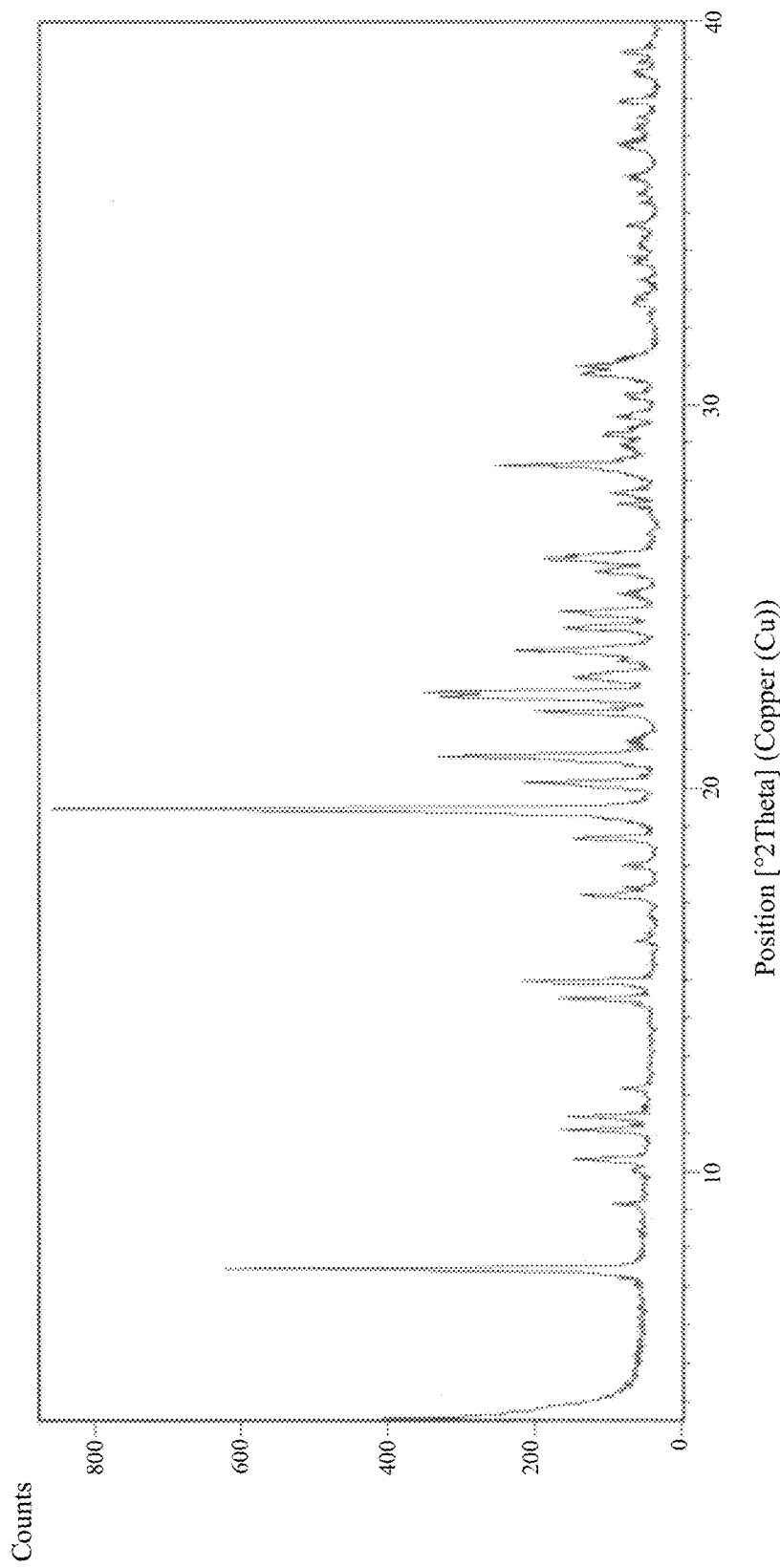
FIG. 2—X-ray powder diffraction pattern of crystalline form L2 of cysteamine bitartrate.

In another embodiment the present invention provides novel crystalline form L2 of cysteamine bitartrate. The crystalline form L2 of cysteamine bitartrate of the present invention is characterized by X-ray powder diffraction pattern as depicted in FIG. 2.

The crystalline form L2 of cysteamine bitartrate having characteristic diffraction peaks 7.4, 10.3, 11.0, 11.4, 14.4, 14.9, 18.6, 19.4, 20.1, 20.8, 21.9, 22.3, 22.5, 23.5±0.2 degree two theta in an X-ray diffraction pattern. The X-ray powder diffraction pattern was recorded at room temperature using PANalytical X'Pert PRO diffractogram with Cu Kα radiation ($\lambda$=1.54060 Å), running at 45 kV and 40 mA.

In yet another embodiment, the present invention provides a process for the preparation of crystalline form L2 of cysteamine bitartrate comprising the steps of:
a) dissolving cysteamine bitartrate in a solvent,
b) optionally adding seed material,
c) cooling the mixture,
d) isolating the solid and
e) drying the solid to obtain crystalline form L2 of cysteamine bitartrate.

Solvents can be selected from organic polar solvent, water or mixtures thereof. Polar solvent can be selected from alcohols like methanol, ethanol, butanol, propanol; nitriles like acetonitrile, propionitrile, butyronitrile; ethers like tetrahydrofuran, dioxane, dimethoxyethane; esters like ethyl acetate, ethyl acetoacetate, butyl acetate, propyl acetate; ketones like acetone, methyl ethyl ketone, methyl isobutyl ketone; other polar solvents like dimethylformamide, dimethyl sulfoxide, water and mixtures thereof.

Cysteamine bitartrate can be dissolved in solvent by heating the mixture of cysteamine bitartrate and the solvent to a temperature of 25° C. to reflux temperature. The seed material can be added at a temperature of 0 to 15° C. The mixture is cooled to a temperature of below 0° C., preferably below −10° C., more preferably below −20° C.; for a period ranging from 30 to 180 minutes and the solid can be isolated by techniques known in art like filtration, concentration, removal of solvent by evaporation, distillation, cooling, flash evaporation, drying on rotavapor. The solid is dried under 800-900 mm/Hg of vacuum at 25-60° C. for a period of 2-24 hours.

It has been observed that crystalline form L2 of cysteamine bitartrate is stable and do not get converted to any other polymorphic form over a period of time and the impurity profile also remains consistent in the hold time study.

Crystalline forms L1 and L2 of cysteamine bitartrate are suitable for preparation of pharmaceutical composition such as tablet, capsule, solution or drops. The pharmaceutical composition containing crystalline forms L1 and L2 of cysteamine bitartrate as the active ingredient along with pharmaceutically acceptable carriers, excipients or diluents can be prepared by methods known in the art. The pharmaceutical compositions containing crystalline form L1 and L2 of cysteamine bitartrate can be used for management of nephropathic cystinosis.

The present invention is further illustrated by the following representative examples and does not limit the scope of the invention.

EXAMPLES

1. Preparation of Cysteamine Bitartrate.

A mixture of ethanol (1000 ml), butylated hydroxy anisole (1 g) and cysteamine hydrochloride (100 g) was stirred and cooled to 5 to 10° C. To this mixture a solution of ethanol (500 ml) and sodium hydroxide (352 g) was added over a period of 30 minutes. The mixture was stirred at a temperature of 10 to 15° C. for 45 minutes. The mixture was filtered through celite. The filtrate was added to a mixture of ethanol (1250 ml), butylated hydroxy anisole (1 g) and L-(+)-tartaric acid (132 g) at a temperature of 55-60° C. The reaction mixture was stirred at 70-75° C. for 45 minutes. The mixture was cooled to 20-30° C. The solid was filtered, washed with ethanol and dried under vacuum.

2. Purification of Cysteamine Bitartrate.

A mixture of cysteamine bitartrate (100 g) and ethanol (5000 ml) was heated to a temperature of 77-82° C. The solution was filtered and the filtrate was cooled to 20 to 30° C. and stirred for 40 minutes. The solid was filtered, washed with ethanol and dried under vacuum. Yield: 80 g; HPLC purity: 99.90%.

3. Preparation of Crystalline Form L1 of Cysteamine Bitartrate.

A mixture of cysteamine bitartrate (50 g) and methanol (600 ml) was heated to a temperature of 35-45° C. The solution was filtered and the filtrate was cooled to 5 to 10° C. Cysteamine bitartrate (0.25 g) seed material was added to the filtrate. The slurry was cooled to −5 to −25° C. and stirred for 40 minutes. The solid was filtered, washed with precooled methanol and dried under vacuum. Yield: 40 g. Cysteamine bitartrate with X-ray powder diffraction pattern as depicted in FIG. 1 was obtained.

4. Preparation of Crystalline Form L2 of Cysteamine Bitartrate.

A mixture of cysteamine bitartrate (50 g), butylated hydroxy anisole (1.3 g) and methanol (600 ml) was heated to a temperature of 35-45° C. The solution was filtered and the filtrate was cooled to 5 to 10° C. Cysteamine bitartrate (0.25 g) seed material was added to the filtrate. The slurry was cooled to −25 to −30° C. and stirred for 40 minutes. The solid was filtered, washed with precooled methanol and the solid was dried under 800-900 mm/Hg of vacuum at 35-40° C. for 5 hours. Yield: 40 g. Cysteamine bitartrate with X-ray powder diffraction pattern as depicted in FIG. 2 was obtained.

The invention claimed is:

1. A crystalline form L1 of cysteamine bitartrate having characteristic diffraction peaks at 10.36, 14.54, 17.23, 18.03, 19.24, 20.76, 21.20, 22.02, 23.37, 23.64, 27.71, 28.28, 29.26, 31.33, 32.84, 33.83, 35.51, 36.74±0.2 degree two theta in an X-ray diffraction pattern.

2. A crystalline form L1 of cysteamine bitartrate according to claim 1, characterized by X-ray powder diffraction pattern as depicted in FIG. 1.

3. The crystalline form L1 of cysteamine bitartrate according to claim 1, having characteristic infrared absorption at 3321, 2975, 2495, 1872, 1730, 1586, 1411, 1336, 1304, 1263, 1213, 1134±2 cm-1.

4. The crystalline form L1 of cysteamine bitartrate according to claim 1, having characteristic differential scanning calorimetry peak at about 75.5° C.

* * * * *